United States Patent
Peyman et al.

(10) Patent No.: US 6,867,213 B2
(45) Date of Patent: Mar. 15, 2005

(54) (2S)-2-(ADAMANTAN-1-YLMETHOXYCARBONYLAMINO)-3-(4-(2-(1,4,5,6-TETRHYDROPYRIMIDIN-2-YLCARBAMOYL)ETHYL)BENZOYLAMINO) PROPIONIC ACID ISOPROPYL ESTER, ITS PREPARATION AND ITS USE

(75) Inventors: Anuschirwan Peyman, Kelkheim (DE); Theodor Wollmann, Haitersheim (DE); Gerhard Brejpohl, Frankfurt am Main (DE); Jean-Francois Gourvest, Claye Souilly (FR); Jean-Marie Ruxer, Issy les Moulineaux (FR); Thomas Gadek, Oakland, CA (US); Robert McDowell, San Francisco, CA (US)

(73) Assignees: Aventis Pharma Deutschland GmbH (DE); Genentech Inc.

( * ) Notice: Subject to any disclaimer, the term of this patent is extended or adjusted under 35 U.S.C. 154(b) by 49 days.

(21) Appl. No.: 10/398,821

(22) PCT Filed: Sep. 27, 2001

(86) PCT No.: PCT/EP01/11186

§ 371 (c)(1),
(2), (4) Date: Jul. 30, 2003

(87) PCT Pub. No.: WO02/30910

PCT Pub. Date: Apr. 18, 2002

(65) Prior Publication Data

US 2004/0039006 A1 Feb. 26, 2004

(30) Foreign Application Priority Data

Oct. 10, 2000 (EP) .............................................. 00121986

(51) Int. Cl.[7] ...................... A61K 31/505; C07D 239/02
(52) U.S. Cl. ....................................... 514/256; 544/297
(58) Field of Search ........................... 514/256; 544/297

(56) References Cited

FOREIGN PATENT DOCUMENTS

| EP | 0820991 | 1/1998 |
|---|---|---|
| WO | 9932457 | 7/1999 |

*Primary Examiner*—Kamal Saeed
(74) *Attorney, Agent, or Firm*—Muserlian, Lucas and Mercanti

(57) ABSTRACT

(2S)-2-(Adamantan-1-ylmethoxycarbonylamino)-3-(4-(2-(1,4,5,6-tetrahydropyrimidin-2-ylcarbamoyl)ethyl) benzoylamino)propionic acid isopropyl ester, its preparation and its use The present invention relates to (2S)-2-(adamantan-1-yl-methoxycarbonylamino)-3-(4-(2-(1,4,5,6-tetrahydropyrimidin-2-ylcarbamoyl)ethyl)benzoylamino)propionic acid isopropyl ester of the formula I

I

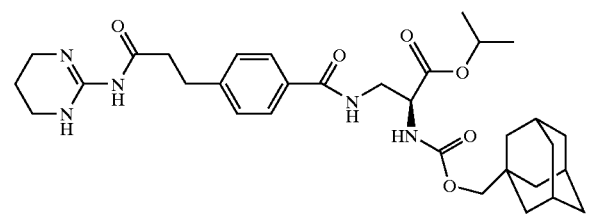

and its physiologically tolerable salts, their preparation, their use as pharmaceuticals and to pharmaceutical compositions comprising them. The compound of the formula I and its physiologically tolerable salts are valuable pharmacologically active compounds which can be used, for example, in the treatment or prophylaxis of diseases which can be influenced by inhibiting the vitronectin receptor, for example of bone diseases such as osteoporosis.

6 Claims, No Drawings

(2S)-2-(ADAMANTAN-1-YLMETHOXYCARBONYLAMINO)-3-(4-(2-(1,4,5,6-TETRHYDROPYRIMIDIN-2-YLCARBAMOYL)ETHYL)BENZOYLAMINO) PROPIONIC ACID ISOPROPYL ESTER, ITS PREPARATION AND ITS USE

This application is a 371 of PCT/FR01/011186 filed Sep. 27, 2001.

The present invention relates to (2S)-2-(adamantan-1-ylmethoxycarbonylamino)-3-(4-(2-(1,4,5,6-tetrahydropyrimidin-2-ylcarbamoyl)ethyl)benzoylamino) propionic acid isopropyl ester of the formula I

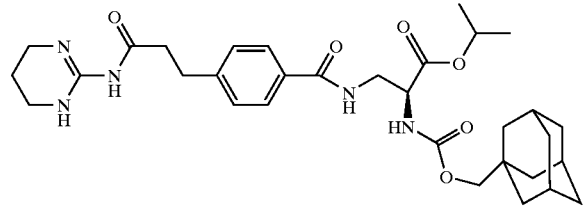

and its physiologically tolerable salts, their preparation, their use as pharmaceuticals and to pharmaceutical compositions comprising them. The compound of the formula I and its physiologically tolerable salts are valuable pharmacologically active compounds which can be used, for example, in the treatment or prophylaxis of diseases which can be influenced by inhibiting the vitronectin receptor, for example of bone diseases such as osteoporosis.

Bones are subject to an ongoing dynamic renovation process comprising bone resorption and bone formation. In certain bone diseases like osteoporosis bone resorption predominates over bone formation thus leading to lower bone mass and enhanced fragility. Bone resorption and bone formation are controlled by types of cell specialized for these purposes. Bone resorption is based on the destruction of bone matrix by osteoclasts. Activated osteoclasts become attached to the surface of the bone matrix and secrete proteolytic enzymes and acids which cause the destruction of the bone. The attachment of osteoclasts to the bones, and thus bone resorption, is controlled by vitronectin receptors $\alpha_v\beta_3$ on the cell surface of osteoclasts. $\alpha_v\beta_3$ in this case binds to bone matrix proteins such as osteopontin, bone sialoprotein and thrombospontin. Antagonists of $\alpha_v\beta_3$ inhibit the attachment of osteoclasts to the bones and thus bone resorption as has been shown, for example, in in vivo experiments described by Fisher et al., Endocrinology 132 (1993) 1411; Yamamoto et al., Endocrinology 139 (1998) 1411; or Miller et al., Bioorg. Med. Chem. Letters 9 (1999) 1807.

The vitronectin receptor $\alpha_v\beta_3$ is a membrane glycoprotein belonging to the superfamily of integrin receptors, and besides on osteoclasts is expressed on the cell surface of other cells such as endothelial cells, cells of the vascular smooth musculature or tumor cells and controls interaction processes in which such cells are involved. In addition to inhibiting bone resorption, $\alpha_v\beta_3$ antagonists are therefore capable of influencing other processes such as tumor growth and metastasis, arteriosclerosis, angiogenesis or inflammation, and in general $\alpha_v\beta_3$ antagonists are suitable for the therapy and prophylaxis of diseases which are based on the interaction between vitronectin receptors and their ligands in cell-cell or cell-matrix interaction processes or which can be prevented, alleviated or cured by influencing this interaction. $\alpha_v\beta_3$ as a therapeutic target and indications for $\alpha_v\beta_3$ antagonists have been reviewed, for example, by Miller et al., Drug Discovery Today 5 (2000) 397.

For example, it has been shown by Yue et al., Pharmacol. Rev. Commun. 10 (1998) 9; or Coleman et al., Circulation Res. 84 (1999) 1268, that $\alpha_v\beta_3$ antagonists inhibit the migration of vascular smooth muscle cells and reduce neointima formation which leads to arteriosclerosis and restenosis after angioplasty.

It has also been shown that the vitronectin receptor $\alpha_v\beta_3$ is involved in the progression of a variety of types of cancer, and that $\alpha_v\beta_3$ antagonists can cause a shrinkage of tumors by inducing the apoptosis of blood vessel cells during angiogenesis and can inhibit tumor growth and tumor metastasis (see, for example, Brooks et al., Cell 79 (1994) 1157; Carron et al., Cancer Res. 58 (1998) 1930; Yun et al., Cancer Res. 56 (1996) 1268; or above-mentioned references). The combination of $\alpha_v\beta_3$ antagonists with other known antitumor treatments has been shown to act highly efficiently on tumors and metastasis (Lode et al., Proc. Natl. Acad. Sci. USA 96 (1999) 1591).

Friedlander et al., Science 270 (1995) 1500, have described $\alpha_v\beta_3$ antagonists which inhibit the bFGF-induced angiogenesis processes in the rat eye, a property which can be used therapeutically in the treatment of retinopathies and psoriasis. Storgard et al., J. Clin. Invest. 103 (1999) 47, have described the use of $\alpha_v\beta_3$ antagonists in the treatment of arthritic diseases.

Influencing the vitronectin receptor $\alpha_v\beta_3$ or the interactions in which it is involved thus offers the possibility of influencing different disease states for whose therapy and prophylaxis there continues to be a need for suitable pharmaceutical active ingredients.

Various integrin antagonists including $\alpha_v\beta_3$ antagonists have already been described, e.g. in EP-A-820991, WO-A-00/47564, WO-A-93/19046, WO-A-94/12181, WO-A-95/32710, WO-A-98/00395, WO-A-98/23451 or WO-A-99/32457. Certain acylguanidine derivatives described in EP-A-820991 and its corresponding applications, for example CA-A-2211270, which are incorporated herein by reference, are particularly strong $\alpha_v\beta_3$ antagonists and inhibitors of bone resorption. Said acylguanidine derivatives include (2S)-2-(adamantan-1-ylmethoxycarbonylamino)-3-(4-(2-(1,4,5,6-tetrahydropyrimidin-2-ylcarbamoyl)ethyl)benzoylamino)propionic acid. It has now been found that (2S)-2(adamantan-1-ylmethoxycarbonylamino)-3-(4-(2-(1,4,5,6-tetrahydropyrimidin-2-ylcarbamoyl)ethyl)benzoylamino)propionic acid isopropyl ester, which in vivo is converted into the actually $\alpha_v\beta_3$ antagonistic (2S)-2-(adamantan-1-ylmethoxycarbonylamino)-3-(4-(2-(1,4,5,6-tetrahydropyrimidin-2-ylcarbamoyl)ethyl)benzoylamino) propionic acid, exhibit an especially favorable pharmacological profile and especially favorable pharmacokinetic characteristics.

Thus, a subject of the present invention is (2S)-2-(adamantan-1-ylmethoxycarbonyl-amino)-3-(4-(2-(1,4,5,6-tetrahydropyrimidin-2-ylcarbamoyl)ethyl)benzoylamino)-propionic acid isopropyl ester of the formula I

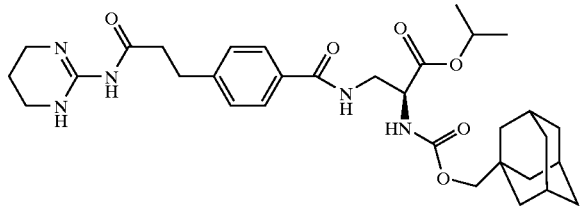

I and its physiologically tolerable salts.

Physiologically tolerable salts of the compound of the formula I which are acid addition salts may be represented by the formula II,

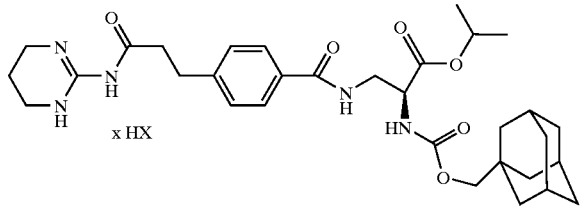

II or equally good, for example, by the formula IIa.

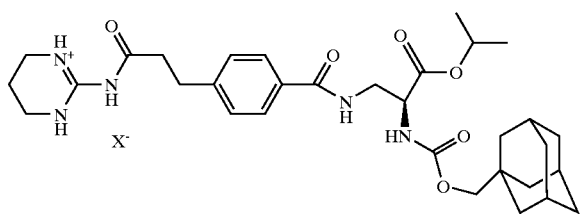

IIa

In formulae II and IIa the acid HX is a physiologically tolerable acid and the anion X is a physiologically tolerable anion, in particular a non-toxic pharmaceutically acceptable anion. HX can be a monobasic or dibasic or tribasic acid, and it can be an organic acid, for example a carboxylic acid or a sulfonic acid, or an inorganic acid. Depending on the specific salt and the details of its preparation, the molar amount of acid per mol of compound of the formula I may vary in the salts according to the invention. In the case of a dibasic acid, for example, one (or about one) acid equivalent per mol of the compound of formula I and thus half (or about half) a mol of acid per mol of the compound of formula I can be present, but just so two (or about two) acid equivalents per mol of the compound of formula I and thus one (or about one) mol of a dibasic acid per mol of the compound of formula I can be present. In the case of a monobasic acid, for example, one (or about one) acid equivalent per mol of the compound of formula I and thus one (or about one) mol of acid per mol of the compound of formula I can be present, but with respect to monobasic acids as well as other acids also other molar ratios of the acid and the compound of the formula I than the mentioned ones, including non-integer ratios, can be present.

Examples of acids HX, from which the salts of the compound of the formula I according to the invention can be formed and the anions of which can represent X⁻ in formula IIa, are acetic acid, adipic acid, citric acid, fumaric acid, gluconic acid, glutaric acid, glycerophosphoric acid, hydrogen chloride (hydrochloric acid), lactic acid, maleic acid, methanesulfonic acid, pamoic acid (1,1'-methylene-bis(2-hydroxy-3-naphthoic acid), phosphoric acid, sulfuric acid, tartaric acid or toluene-4-sulfonic acid.

In the formulae I, II and IIa a specific tautomeric form is given. The invention covers (2S)-2-(adamantan-1-ylmethoxycarbonylamino)-3-(4-(2-(1,4,5,6-tetrahydropyrimidin-2-ylcarbamoyl)ethyl)benzoylamino) propionic acid isopropyl ester and its physiologically tolerable salts in any tautomeric form including, for example, the forms of formulae Ia and IIb.

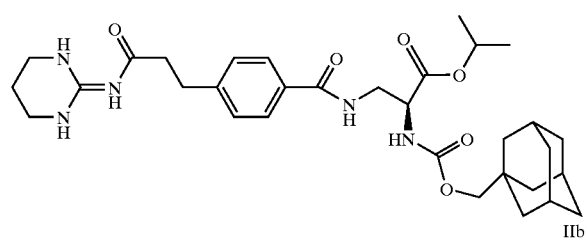

Ia

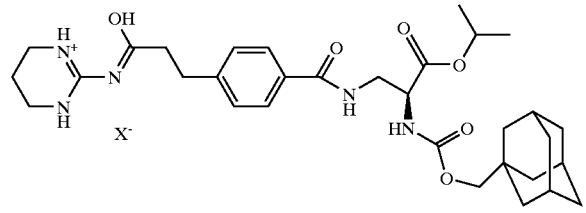

IIb

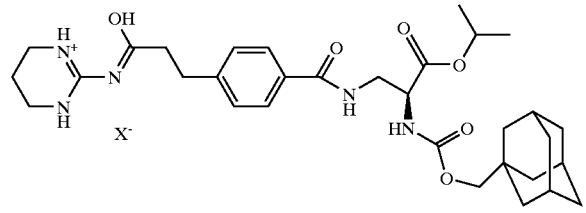

The invention also covers solvates of (2S)-2-(adamantan-1-ylmethoxycarbonylamino)-3-(4-(2-(1,4,5,6-tetrahydropyrimidin-2-ylcarbamoyl)ethyl)benzoylamino) propionic acid isopropyl ester and its physiologically tolerable salts, for example hydrates or adducts with alcohols.

In a preferred embodiment the present invention is directed to the acid addition salt of the compound of formula I with hydrochloric acid which contains the compound of formula I and hydrogen chloride in a molar ratio of 1:1 (or about 1:1), i.e. to (2S)-2-(adamantan-1-ylmethoxycarbonylamino)-3-(4-(2-(1,4,5,6-tetrahydropyrimidin-2-ylcarbamoyl)ethyl)benzoylamino) propionic acid isopropyl ester hydrochloride which is the compound of formula II wherein HX is HCl and the compound of formula IIa wherein the anion X is the chloride anion, respectively. This preferred subject of the invention can be represented by the formula IIc,

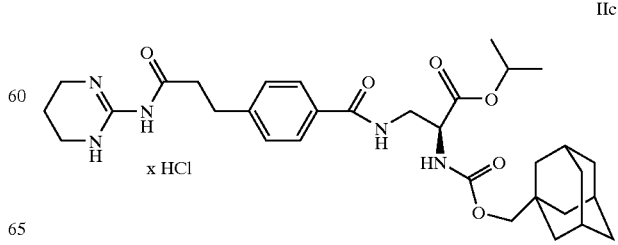

IIc or equally good, for example, by the formula IId.

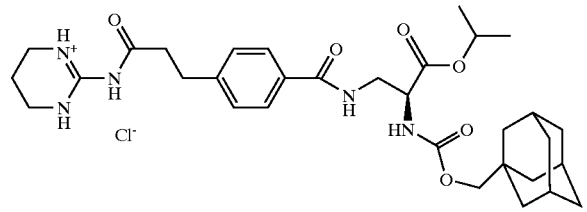

IId

This hydrochloride salt of (2S)-2-(adamantan-1-ylmethoxycarbonylamino)-3-(4-(2-(1,4,5,6-tetrahydropyrimidin-2-ylcarbamoyl)ethyl)benzoylamino) propionic acid isopropyl ester is distinguished by particularly advantageous physicochemical properties like non-hygroscopicity, stability and crystallinity, which could not be foreseen. These physicochemical properties allow an easy handling without special precautionary measures or an expensive special equipment and are of particular advantage in the industrial large scale production of the drug substance and its storage and processing to pharmaceutical compositions. Especially important is the fact that in view of its good crystallization behavior the hydrochloride salt of the compound of the formula I can be easily isolated by crystallization, and if a purification is desired it can easily be recrystallized under defined conditions, for example from ethanol. For the use of a pharmacologically active drug substance in pharmaceuticals the legislator stipulates precisely defined degrees of purity, and in the processes for preparing, isolating and purifying a drug substance likewise conditions and operating procedures have to be adhered to which are precisely defined by legal guidelines. The hydrochloride salt of the compound of formula I makes it possible to adhere with ease to the required degrees of purity and to fulfill the legal demands, as well as the technical demands associated with an industrial synthesis and the galenic demands.

(2S)-2-(Adamantan-1-ylmethoxycarbonylamino)-3-(4-(2-(1,4,5,6-tetrahydropyrimidin-2-ylcarbamoyl)ethyl)benzoylamino)propionic acid isopropyl ester or a salt thereof can be prepared, for example, from (2S)-2-(adamantan-1-ylmethoxycarbonylamino)-3-(4-(2-(1,4,5,6-tetrahydropyrimidin-2-ylcarbamoyl)ethyl)benzoylamino) propionic acid or a salt thereof by conventional methods of esterification known to those skilled in the art. A process for the preparation of (2S)-2-(adamantan-1-ylmethoxycarbonylamino)-3-(4-(2-(1,4,5,6-tetrahydropyrimidin-2-ylcarbamoyl)ethyl)benzoylamino) propionic acid isopropyl ester or a physiologically tolerable salt thereof, comprising esterification of (2S)-2-(adamantan-1-ylmethoxycarbonylamino)-3-(4-(2-(1,4,5,6-tetrahydropyrimidin-2-ylcarbamoyl)ethyl)benzoylamino) propionic acid or a salt thereof with isopropanol, is a further subject of the present invention. Salts of (2S)-2-(adamantan-1-ylmethoxycarbonylamino)-3-(4-(2-(1,4,5,6-tetrahydropyrimidin-2-ylcarbamoyl)ethyl)benzoylamino) propionic acid which can be employed in the esterification include addition salts with acids, for example the above-mentioned acids HX, metal salts of the carboxylic acid group, for example alkali metal salts or alkaline earth metal salts, and the inner salt (or betain) in which a carboxylate anion and a protonated guanidino moiety are present.

The esterification can be carried out, for example, by conversion of the carboxylic acid group into an reactive carboxylic acid derivative and subsequent reaction with isopropanol. Preferably the isopropyl ester is prepared by acidic esterification of (2S)-2-(adamantan-1-ylmethoxycarbonylamino)-3-(4-(2-(1,4,5,6-tetrahydropyrimidin-2-ylcarbamoyl)ethyl)benzoylamino) propionic acid or a salt thereof with isopropanol, e.g. by treatment with isopropanol and an acid such as, for example, hydrogen chloride or sulfuric acid, or by treatment with isopropanol and thionyl chloride. For the preparation of the free isopropyl ester of the formula I the work-up of the reaction mixture may then include a neutralization with a suitable base, for example sodium hydrogencarbonate. Details of esterification reactions can be found in standard references like Houben-Weyl, Methoden der organischen Chemie (Methods of Organic Chemistry), Georg Thieme Verlag, Stuttgart; or J. March, Advanced Organic Chemistry, Third Edition, John Wiley & Sons, 1985, and the literature quoted therein. For example, the esterification with isopropanol in the presence of sulfuric acid is favorably carried out by heating (2S)-2-(adamantan-1-ylmethoxycarbonylamino)-3-(4-(2-(1,4,5,6-tetrahydropyeimidin-2-ylcarbamoyl)ethyl) benzoylamino)propionic acid and sulfuric acid in excess isopropanol, for example to a temperature of about 70 to about 90° C., preferably by heating under atmospheric pressure to reflux temperature.

The starting compound (2S)-2-(adamantan-1-ylmethoxycarbonylamino)-3-(4-(2-(1,4,5,6-tetrahydropyrimidin-2-ylcarbamoyl)ethyl)benzoylamino) propionic acid can be prepared according to the method described in EP-A-820991 and corresponding patent documents.

Physiologically tolerable salts of (2S)-2-(adamantan-1-ylmethoxycarbonylamino)-3-(4-(2-(1,4,5,6-tetrahydropyrimidin-2-ylcarbamoyl)ethyl)benzoylamino) propionic acid isopropyl ester can be prepared according to conventional procedures, for example by combining the free (2S)-2-(adamantan-1-ylmethoxycarbonylamino)-3-(4-(2-(1,4,5,6-tetrahydropyrimidin-2-ylcarbamoyl)ethyl) benzoylamino)propionic acid isopropyl ester of formula I with the respective acid HX in a solvent or diluent. Examples of suitable solvents or diluents are water, alcohols such as methanol, ethanol or isopropanol, ethers such as dioxane, tetrahydrofuran, ethylene glycol monomethyl ether, ethylene glycol dimethyl ether, diethylene glycol monomethyl ether or diethylene glycol dimethyl ether, or ketones such as acetone or butanone, as well as mixtures of two or more of these solvents. The salt formation is normally carried out at temperatures of from about −10 to about 100° C., preferably of from about −10 to about 80° C., more preferably of from about −5 to about 30° C., particularly preferably of from about 0 to about 25° C. Depending on the individual case, it can be favorable to employ the acid HX in the desired stoichiometric amount or approximately the desired stoichiometric amount, or in a small excess or a greater excess. Besides from the free compound of the formula I and an acid, salts can also be directly obtained in the above-described esterification of (2S)-2-(adamantan-1-ylmethoxycarbonylamino)-3-(4-(2-(1,4,5,6-tetrahydropyrimidin-2-ylcarbamoyl)ethyl)benzoylamino) propionic acid or a salt thereof with isopropanol. If said esterification is carried out in the presence of an acid, the addition salt with that acid will be formed and can be isolated, if desired.

Specifically the hydrochloride of (2S)-2-(adamantan-1-ylmethoxycarbonylamino)-3-(4-(2-(1,4,5,6-tetrahydropyrimidin-2-ylcarbamoyl)ethyl)benzoylamino) propionic acid isopropyl ester, i.e. the compound of the formula IIc, can be obtained, for example, by combining the free compound of formula I with about an equimolar amount of hydrogen chloride or an excess molar amount of hydrogen chloride, for example about 1 to about 1.5 mol of hydrogen chloride per mol of the compound of formula I, in a solvent or diluent, for example water or an alcohol like methanol or ethanol. Favorably the hydrochloride of the formula II can also be obtained directly in the esterification of (2S)-2-(adamantan-1-ylmethoxycarbonylamino)-3-(4-(2-(1,4,5,6-tetrahydropyrimidin-2-ylcarbamoyl)ethyl) benzoylamino)propionic acid with isopropanol and thionyl chloride.

A physiologically tolerable salt of (2S)-2-(adamantan-1-ylmethoxycarbonylamino)-3-(4-(2-(1,4,5,6-tetrahydropyrimidin-2-ylcarbamoyl)ethyl)benzoylamino) propionic acid isopropyl ester can also be prepared from another salt by anion exchange. Such other salt may be a synthetic intermediate that has been obtained in the above-described esterification process or in another process leading to a salt of the compound of the formula I. As starting material in an anion exchange process also salts of low physiological tolerability can be employed which are not directly suitable for use as pharmaceuticals. A further subject of the present invention, besides the physiologically tolerable salts of the compound of the formula I, are also salts of the compound of the formula I which exhibit a low physiological tolerability but which are suitable as starting materials for the preparation of physiologically tolerable salts or as synthetic intermediates for any chemical modification of the compound of the formula I.

Suitable anion exchange processes for the conversion of a salt of the compound of the formula I into another salt include anion exchange chromatography and anion exchange in solution or suspension. The following details on these techniques exemplarily refer to the preparation of the hydrochloride of the formula IIc, but they analogously apply to the preparation of other salts by anion exchange. For the preparation of the hydrochloride salt of the formula IIc a solution of another salt of (2S)-2-(adamantan-1-ylmethoxycarbonylamino)-3-(4-(2-(1,4,5,6-tetrahydropyrimidin-2-ylcarbamoyl)ethyl)benzoylamino) propionic acid isopropyl ester can be chromatographed through an ion-exchange material in the chloride form. Commercially available anion-exchange materials can be employed which have prior to use been loaded with chloride by treatment with hydrochloric acid or a chloride salt as is customary, or which have been regenerated into the chloride form in the case of repeated use. Examples of suitable solvents for such an anion exchange chromatography are water and alcohols such as methanol, ethanol, n-butanol or i-propanol, and mixtures of these solvents, for example mixtures of water and methanol and/or ethanol. The anion exchange chromatography is normally carried out at temperatures of from about −10 to about 40° C., preferably of from about −5 to about 30° C., more preferably of from about 0 to about 25° C.

For the anion exchange, also a solution or suspension of another salt of (2S)-2-(adamantan-1-ylmethoxycarbonylamino)-3-(4-(2-(1,4,5,6-tetrahydropyrimidin-2-ylcarbamoyl)ethyl)benzoylamino) propionic acid isopropyl ester in a solvent or diluent can be brought into contact with hydrogen chloride (hydrochloric acid) and/or chlorides, usually with stirring. The other salt of (2S)-2-(adamantan-1-ylmethoxycarbonylamino)-3-(4-(2-(1, 4,5,6-tetrahydropyrimidin-2-ylcarbamoyl)ethyl) benzoylamino)propionic acid isopropyl ester can be initially introduced and the hydrochloric acid or one or more chlorides, for example metal chlorides like alkali metal or alkaline earth metal chlorides or ammonium chlorides including quaternary ammonium chlorides, be added, or mixtures of hydrochloric acid and one or more chlorides can be added. Vice versa there can first be introduced hydrochloric acid and/or chlorides and then the other salt of the compound of formula I be added, or both components can also simultaneously be metered into the reaction vessel. While the components can be brought into contact in the form of solutions, it can, depending on specific salt and the manner in which the anion exchange is performed, also be advantageous to initially introduce suspensions and/or to add suspensions or solids.

Examples of suitable solvents or diluents for an anion exchange in solution or suspension are water, alcohols, for example alcohols having from 1 to 8 carbon atoms, preferably alcohols having from 1 to 6 carbon atoms, more preferably alcohols having from 1 to 4 carbon atoms, ethers such as dioxane, tetrahydrofuran, ethylene glycol monomethyl ether, ethylene glycol dimethyl ether, diethylene glycol monomethyl ether or diethylene glycol dimethyl ether, ketones such as acetone or butanone, nitriles such as acetonitrile, dimethylformamide or dimethyl sulfoxide. Examples of alcohols which can be employed are methanol, ethanol, n-propanol, isopropanol, n-butanol, isobutanol, sec-butanol, tert-butanol, n-pentanol, isopentanol, tert-pentanol, n-hexanol, 2-ethylbutanol, 2-ethylhexanol, isooctanol, cyclopentanol, methylcyclohexanol (mixture) or benzyl alcohol. Also mixtures of two or more solvents (or diluents), including two-phase mixtures, can be used, for example mixtures of water and alcohols like water and methanol or water and ethanol. The anion exchange in solution or suspension is normally carried out at temperatures of from about −10 to about 40° C., preferably of from about −5 to about 30° C., more preferably of from about 0 to about 25° C.

For the isolation of the resulting product salt from the mixture obtained after salt formation of the compound of the formula I with an acid, or after anion exchange chromatography or anion exchange in solution or suspension, standard procedures can be employed. If desired, the mixture or eluate can be concentrated and/or cooled and/or admixed with another solvent in order to cause crystallization or precipitation. The product salt can then be separated off by means of filtration or centrifugation. The isolation of the product salt can also take place by lyophilization. Depending on the requirements, the isolated salt can then additionally be washed and, if desired, be subjected to further purification, for example by means of recrystallization.

The compound of the formula I and its physiologically tolerable salts, in particular the hydrochloride salt of formula IIc are valuable pharmacologically active compounds which are suitable, for example, for the therapy and prophylaxis of bone disorders, tumor diseases, cardiovascular disorders or inflammatory conditions or ocular diseases. They can be administered to animals, preferably to mammals, and in particular to humans as a pharmaceutical for therapy or prophylaxis. They can be administered on its own or in mixture with other pharmacologically active compounds or in the form of pharmaceutical compositions which permit enteral or parenteral administration and which, as active constituent, contain an efficacious dose of the compound of the formula I and/or a physiologically tolerable salt thereof, in particular the hydrochloride salt of formula IIc.

The present invention therefore also relates to the compound of the formula I and its physiologically tolerable salts, in particular the hydrochloride salt of formula IIc, for use as a pharmaceutical, to their use for the production of pharmaceuticals for the therapy and prophylaxis of the diseases mentioned above or below, for example for the therapy and prophylaxis of bone disorders, tumor diseases, cardiovascular disorders or inflammatory conditions or ocular diseases, and also to the use of the compound of the formula I and its physiologically tolerable salts, in particular the hydrochloride salt of formula IIc, for the therapy and prophylaxis of these diseases and to methods for such therapy and prophylaxis. The present invention furthermore relates to pharmaceutical compositions (or pharmaceutical preparations) which contain an efficacious dose of the compound of the formula I and/or its physiologically tolerable salts, in particular the hydrochloride salt of formula IIc, and a pharmaceutically acceptable carrier, i.e. one or more pharmaceutically acceptable carrier substances and/or additives.

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions emulsions or tinctures, or in other ways, for example in the form of aerosols or nasal sprays.

The pharmaceutical compositions according to the invention can be prepared in a manner known per se and familiar to those skilled in the art, the compound of the formula I and/or its physiologically tolerable salts, in particular the hydrochloride salt of formula IIc, being mixed with one or more pharmaceutically acceptable inert inorganic and/or organic carrier substances (or excipients) and/or additives and, if desired, one or more other pharmaceutically active compounds and being brought into a suitable administration form and dosage form that can be used in human or veterinary medicine. For the production of pills, tablets, coated tablets and hard gelatin capsules it is possible to use, for example, lactose, corn starch or derivatives thereof, talc, stearic acid or its salts, etc. Carrier substances for soft gelatin capsules and suppositories are, for example, fats, waxes, semisolid and liquid polyols, natural or hardened oils, etc. Suitable carrier substances for the production of solutions, for example injection solutions, or of emulsions or syrups are, for example, water, alcohols, glycerol, polyols, sucrose, invert sugar, glucose, vegetable oils, etc. Suitable carrier substances for microcapsules, implants or rods are, for example, copolymers of glycolic acid and lactic acid. The pharmaceutical compositions normally contain about 0.5 to about 90% by weight of the compound of the formula I. The amount of the active ingredient of the formula I and/or its physiologically tolerable salts, in particular the hydrochloride salt of formula IIc, in the pharmaceutical compositions normally is from about 0.2 mg to about 500 mg, preferably from about 1 mg to about 200 mg, per dose unit, but depending on the type of the pharmaceutical composition it may also be higher.

In addition to the active ingredient of the formula I and/or its physiologically tolerable salts, in particular the hydrochloride salt of formula IIc, and carrier substances, the pharmaceutical compositions can contain additives (or auxiliary substances) such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. Furthermore, in addition to the compound of the formula I and/or its physiologically tolerable salts, in particular the hydrochloride salt of formula IIc, they can also contain one or more other therapeutically or prophylactically active ingredients.

The compound of the formula I and its physiologically tolerable salts, in particular the hydrochloride salt of formula IIc, in vivo are antagonists of the vitronectin receptor and inhibit cell adhesion. They have, for example, the ability to inhibit the binding of osteoclasts to the bone surface and thereby inhibit bone resorption by osteoclasts. This action can be demonstrated, for example, in the test described below. Because of its vitronectin receptor antagonistic activity the compound of the formula I and its physiologically tolerable salts are generally suitable for the therapy and prophylaxis of diseases which are based on the interaction between vitronectin receptors and their ligands in cell-cell interaction processes or cell-matrix interaction processes, or which can be influenced by an inhibition of interactions of this type, or for the prevention, alleviation or cure of which an inhibition of interactions of this type is desired. As explained at the beginning, such interactions play a part, for example, in bone resorption, in angiogenesis or in the proliferation of cells of the vascular smooth musculature. The compound of the formula I and its physiologically tolerable salts, in particular the hydrochloride salt of formula IIc, are therefore suitable, for example, for the prevention, alleviation or cure of diseases which are caused at least partially by an undesired extent of bone resorption, angiogenesis or proliferation of cells of the vascular smooth musculature.

Bone diseases for whose treatment and prevention the compound of the formula I and its physiologically tolerable salts, in particular the hydrochloride salt of formula IIc, can be employed are especially osteoporosis, hypercalcemia, osteopenia, for example caused by metastases, dental disorders, hyperparathyroidism, periarticular erosions in rheumatoid arthritis and Paget's disease. In addition, the compound of the formula I and its physiologically tolerable salts, in particular the hydrochloride salt of formula IIc, can be used for the alleviation, avoidance or therapy of bone disorders which are caused by a glucocorticoid, steroid or corticosteroid therapy or by a lack of sex hormone(s). All these disorders are characterized by bone loss which is based on the inequilibrium between bone formation and bone destruction and which can be favorably influenced by the inhibition of bone resorption by osteoclasts. The compound of the formula I and/or its physiologically tolerable salts, in particular the hydrochloride salt of formula IIc, can also favorably be used as inhibitor of bone resorption, for example in the therapy or prophylaxis of osteoporosis, in combination with conventional osteoporosis treatments such as, for example, and the administration of bisphosphonates, estrogens, estrogen/progesterone (hormone replacement therapy or HRT), estrogen agonists/antagonists (selective estrogen receptor modulators or SERMs), calcitonin, vitamin D analogues, parathyroid hormone, growth hormone secretagogues, or sodium fluoride (cf. Jardine et al., Annual Reports in Medicinal Chemistry 31 (1996) 211). Administration of the compound of the formula I and/or its physiologically tolerable salts, in particular the hydrochloride salt of formula IIc, and of other active ingredients effective in the treatment or prophylaxis of osteoporosis like those listed before can take place simultaneously or sequentially, in any order, and jointly or separately. For use in such a combination treatment or prophylaxis the compound of the formula I and/or its physiologically tolerable salts, in particular the hydrochloride salt of formula IIc, and one or more other active ingredients like those listed before can together be present in a single pharmaceutical composition, for example tablets, capsules or granules, or can be present in two or more separate pharmaceutical compositions which can be contained in a single package or in two or more separate packages. The use of the compound of the formula I and/or its physiologically tolerable salts, in particular the hydrochloride salt of formula IIc, in such a combination therapy or prophylaxis and their use in the production of pharmaceuticals for such a combination therapy or prophylaxis are also subjects of the present invention. The invention furthermore relates to pharmaceutical compositions which comprise an efficacious amount of the compound of the formula I and/or its physiologically tolerable salts, in particular the hydrochloride salt of formula IIc, together with at least one other active ingredient effective in the treatment or prophylaxis of osteoporosis or in the inhibition of bone resorption like those listed before, together with a customary pharmaceutically acceptable carrier. The above explanations on pharmaceutical compositions correspondingly apply to such pharmaceutical combination compositions.

Apart from use as inhibitors of bone resorption by osteoclasts, the compound of the formula I and/or its physiologically tolerable salts, in particular the hydrochloride salt of formula IIc, can be used, for example, as inhibitors of tumor growth and tumor metastasis, as antiinflammatories, for the therapy or prophylaxis of rheumatoid arthritis, for the therapy of psoriasis, for the therapy or prophylaxis of cardiovascular disorders such as arteriosclerosis or restenoses, for the therapy or prophylaxis of nephropathies or retinopathies such as, for example, diabetic retinopathy, or of age-related macular degeneration. As inhibitor of tumor growth or tumor metastasis the compound of the formula I and/or its physiologically tolerable salts, in particular the hydrochloride salt of formula IIc, can also favorably be used in combination with conventional cancer therapy. Examples of conventional cancer therapy are given in Bertino (Editor), Encyclopedia of Cancer, Academic Press, 1997 which is incorporated herein by reference. All the above statements relating to the use of the compound of formula I in combination with conventional osteoporosis therapy like, for example, possible modes of administration and pharmaceutical combination compositions, correspondingly apply to the use of the compound of formula I in combination with conventional cancer therapy.

When using the compound of the formula I and/or its physiologically tolerable salts, in particular the hydrochloride salt of formula IIc, the dose can vary within wide limits and, as is customary, is to be suited to the individual conditions in each individual case. It depends, for example, on the nature and severity of the disease and the general state of the individual to be treated, or on whether an acute or chronic condition is treated or whether prophylaxis is carried out. In the case of oral administration, the daily dose is in general from about 0.01 to about 100 mg/kg, preferably from about 0.1 to about 50 mg/kg, in particular from about 0.1 to about 5 mg/kg, to achieve effective results in an adult weighing about 75 kg (in each case in mg per kg of body weight). Also in the case of intravenous administration the daily dose is in general from about 0.01 to about 100 mg/kg, preferably from about 0.05 to about 10 mg/kg (in each case in mg per kg of body weight). The daily dose can be divided, in particular in the case of the administration of relatively large amounts, into several, for example 2, 3 or 4 part administrations. As usual, depending on individual behavior it may be necessary to deviate upwards or downwards from the daily dose indicated.

The compound of the formula I and its salts, in particular the hydrochloride salt of formula IIc, can furthermore be employed for diagnostic purposes, for example in in vitro diagnoses, or as auxiliary in pharmacological or biochemical investigations in which blocking of the vitronectin receptor or influencing of cell-cell or cell-matrix interactions is desired.

EXAMPLES 1) (2S)-2-(Adamantan-1-ylmethoxycarbonylamino)-3-(4-(2-(1,4,5,6-tetrahydropyrimidin-2-ylcarbamoyl)ethyl)benzoylamino)propionic Acid Isopropyl Ester Acetic Acid Salt 17.5 g of (2S)-2-(adamantan-1-ylmethoxycarbonylamino)-3-(4-(2-(1,4,5,6-tetrahydropyrimidin-2-ylcarbamoyl)ethyl)benzoylamino)propionic acid were dissolved in 670 ml of isopropanol. 1.8 ml of concentrated sulfuric acid were added and the reaction mixture was refluxed for 24 h. The solvent was distilled off in vacuo, the residue was brought to pH 7 with an aqueous solution of sodium chloride and solid sodium bicarbonate and the mixture was extracted four times with ethyl acetate. The combined organic phases were dried over magnesium sulfate, the ethyl acetate was distilled off, the residue was treated with 20 ml of glacial acetic acid and lyophilized.

Yield: 11.2 g.

MS (ES$^+$): m/e=596.4 (M+H$^+$, 100%).

$^1$H-NMR (200 MHz, DMSO-D$_6$): δ (ppm)=1.03–1.29 (m, 6H); 1.39–2.00 (m, 19H); 1.91 (s, 3H); 2.45 (t, 2H); 2.83 (t, 2H); 3.16–3.64 (m, 5H); 3.22 (dd, 4H); 4.21 (dt, 1H); 4.84 (hep, 1H); 7.29 (d, 2H); 7.46 (d, 1H); 7.70 (d, 2H); 8.40 (t, 1H).

2) (2S)-2-(Adamantan-1-ylmethoxycarbonylamino)-3-(4-(2-(1,4,5,6-tetrahydropyrimidin-2-ylcarbamoyl)ethyl)benzoylamino)propionic Acid Isopropyl Ester Hydrochloride 13.0 g of (2S)-2-(adamantan-1-ylmethoxycarbonylamino)-3-(4-(2-(1,4,5,6-tetrahydropyrimidin-2-ylcarbamoyl)ethyl)benzoylamino)propionic acid were dissolved in 500 ml of isopropanol. 1.3 ml of concentrated sulfuric acid were added and the reaction mixture was refluxed for 18 h. The solvent was distilled off in vacuo, the residue was suspended in ethyl acetate and brought to pH 7 with an aqueous solution of sodium chloride and solid sodium bicarbonate. The phases were separated and the organic phase was dried over magnesium carbonate, the ethyl acetate was distilled off, the residue was treated with 25 ml of 2M hydrochloric acid and stirred vigorously for 2 h. The product was filtered, washed with water and dried. The compound was recrystallized from ethanol. Yield: 9.6 g.

Melting point: 208–210° C.

MS (ES$^+$): m/e=596.5 (M+H$^+$, 100%).

3) Preparation of the Starting Compound (2S)-2-(adamantan-1-ylmethoxycarbonylamino)-3-(4-(2-(1,4,5,6-tetrahydropyrimidin-2-ylcarbamoyl)ethyl)benzoylamino) propionic Acid The starting compound employed in examples 1 and 2 can be obtained by the procedure disclosed in EP-A-820991 and described in the following.

a) 4-(2-Methoxycarbonylvinyl)benzoic Acid 18.74 g (0.12 mol) of potassium monomethyl malonate were suspended in 18 ml of pyridine. 15.01 g (0.1 mol) of 4-carboxybenzaldehyde and 0.85 g (0.01 mol) of piperidine were added at room temperature with stirring and the mixture was boiled under reflux until the evolution of carbon dioxide had ceased (about 2 h). A further 60 ml of pyridine were added and the mixture was stirred under reflux for a further 1 h. The reaction mixture was treated with stirring with 500 ml of ice and 110 ml of concentrated hydrochloric acid. After the addition was complete, the mixture was stirred for a further 20 min, and the product was filtered off with suction, washed with water and recrystallized from isopropanol. Yield: 12.85 g (62%).

b) 4-(2-Methoxycarbonylethyl)benzoic Acid 8 g (38.8 mmol) of 4-(2-methoxycarbonylvinyl)benzoic acid (step a) were suspended in 250 ml of dioxane and hydrogenated under 1 bar of hydrogen over palladium/charcoal (10%) at room temperature for 7 h. The mixture was filtered and the solvent was evaporated in vacuo. Yield: 8.05 g (100%).

c) tert-Butyl (2S)-2-benzyloxycarbonylamino-3-(4-(2-methoxycarbonylethyl)benzoylamino)propionate 354 mg (1.7 mmol) of 4-(2-methoxycarbonylethyl)benzoic acid (step b) and 500 mg (1.7 mmol) of tert-butyl (2S)-2-benzyloxycarbonylamino-3-aminopropionate were dissolved in 3 ml of dimethylformamide and treated with 557 mg (1.7 mmol) of O-((cyano(ethoxycarbonyl)methylene)amino)-1,1,3,3-tetramethyluronium tetrafluoroborate (TOTU) and 204 mg (1.7 mmol) of diisopropylethylamine and the solution was stirred at room temperature for 7 h. The solvent was evaporated in vacuo, the residue was dissolved in ethyl acetate and washed three times each with a solution of potassium hydrogen sulfate and a solution of sodium bicarbonate until neutral. The organic phase was separated off and dried, and the solvent was distilled off in vacuo. Yield: 770 mg (93%).

d) tert-Butyl (2S)-2-benzyloxycarbonylamino-3-(4-(2-(1,4,5,6-tetrahydro-pyrimidin-2-ylcarbamoyl)ethyl)benzoylamino)propionate 1.25 g (9.2 mmol) of 2-amino-1,4,5,6-tetrahydropyrimidine hydrochloride and 1.03 g (9.2 mmol) of potassium tert-butoxide were dissolved in 3 ml of absolute dimethylformamide and the mixture was stirred at room temperature for 30 min. 740 mg (1.53 mmol) of tert-butyl (2S)-2-benzyloxycarbonylamino-3-(4-(2-methoxycarbonylethyl)benzoylamino)propionate (step c) in 1 ml of dimethylformamide were then added and the mixture was stirred at room temperature for 4 h. It was then adjusted to pH 4 using glacial acetic acid, the solvent was stripped off in vacuo, and the residue was chromatographed on silica gel (dichloromethane/methanol/glacial acetic acid/water (9/1/0.1/0.1)). Yield: 190 mg (38%).

e) (2S)-2-Benzyloxycarbonylamino-3-(4-(2-(1,4,5,6-tetrahydropyrimidin-2ylcarbamoyl)ethyl)benzoylamino) propionic Acid 190 mg (0.34 mmol) of tert-butyl (2S)-2-benzyloxycarbonylamino-3-(4-(2-(1,4,5,6tetrahydropyrimidin-2-ylcarbamoyl)ethyl)benzoylamino)propionate (step d) were dissolved in 5 ml of 95% trifluoroacetic acid and the mixture was stirred at room temperature for 1 h. The trifluoroacetic acid was distilled off in vacuo and the mixture was co-evaporated with toluene. The residue was dissolved in glacial acetic acid, and the solution was diluted with water and freeze-dried.

Yield: 170 mg (100 %).

f) (2S)-2-Amino-3-(4-(2-(1,4,5,6-tetrahydropyrimidin-2-ylcarbamoyl)ethyl)benzoylamino)propionic Acid 100 mg (0.2 mmol) of (2S)-2-benzyloxycarbonylamino-3-(4-(2-(1,4,5,6-tetrahydropyrimidin-2-ylcarbamoyl)ethyl)benzoylamino)propionic acid (step e) were dissolved in 15 ml of dioxane, treated with 0.012 ml of glacial acetic acid and hydrogenated at room temperature under 1 bar of hydrogen over palladium/charcoal (5%). After 2 h, 15 ml of methanol were added and the mixture was hydrogenated at room temperature under 1 bar of hydrogen for further 5 h. It was then filtered and the solvent was evaporated in vacuo. Yield: 67.4 mg (93%).

g) (2S)-2-(Adamantan-1-ylmethoxycarbonylamino)-3-(4-(2-(1,4,5,6-tetrahydropyrimidin-2-ylcarbamoyl)ethyl)benzoylamino)propionic Acid 67.4 mg (0.186 mmol) of (2S)-2-amino-3-(4-(2-(1,4,5,6-tetrahydropyrimidin-2-ylcarbamoyl)ethyl)benzoylamino)propionic acid (step f) were dissolved in 4 ml of dioxane. With stirring, first 4 ml of saturated solution of sodium bicarbonate and then 57 mg of adamantan-1-ylmethyl 2,5-dioxopyrrplidin-1-yl carbonate were added at room temperature. The mixture was stirred at room temperature for 24 h and adjusted to pH 4 using glacial acetic acid, the solvent was stripped off in vacuo and the residue was chromatographed (20% (v/v) acetonitrile in water, 0.1% trifluoroacetic acid, up to 40% (v/v) acetonitrile) on RP18 Lichrospher C-18. Yield: 30 mg (30%).

3) Pharmacological Testing: PTH-Induced Hypercalcemia in the TPTX Rat Model of Bone Resorption In this in vivo model a stimulation of bone resorption is induced in thyroparathyroidectomized (TPTX) rats by the infusion of parathyroid hormone (PTH). The changes in bone resorption are monitored by measuring the serum calcium concentration which is directly related to the extent of bone resorption.

Male Sprague Dawley rats (OFA-IFFA CREDO, France) weighting 150–200 g were thyroparathyroidectomized by the supplier. The rats were allowed free access to a standard commercial pelleted diet containing 7 g Ca/kg (UAR) and Eau de Volvic water. The success of thyroparathyroidectomy was tested by measuring serum calcium concentrations 8 days after operation in overnight fasted animals. Rats were considered as TPTX when the serum calcium level was <80 mg/l.

For treatment with PTH, rat PTH(1–34) (Bachem) was dissolved in 0.15 M sodium chloride solution containing 2% Cys-HCl and delivered via osmotic minipumps (ALZET 2001D) at 200 pmol/kg/h. The minipumps were inserted into the intraperitoneal cavities under ketamin (75 mg/kg) and acepromazin (2.5 mg/kg) anesthesia in overnight fasted TPTX rats. In the control group TPTX rats received minipumps filled with the vehicle of PTH.

To determine the pharmacological effect of (2S)-2-(adamantan-1-ylmethoxycarbonylamino)-3-(4-(2-(1,4,5,6-tetrahydropyrimidin-2-ylcarbamoyl)ethyl)benzoylamino) propionic acid isopropyl ester, PTH treated TPTX rats were administered twice 30 mg/kg of the hydrochloride of the formula IIc subcutaneously at time 0 and 3 h after the start of PTH infusion (compound group). In the same manner PTH treated TPTX rats were administered the vehicle (PTH group), and TPTX rats not treated with PTH were administered the vehicle (control group). The experiment was performed for a total of 6 hours. At the end of the treatment protocol, whole blood was collected after decapitation. The blood samples were centrifugated at 3000 rpm for 15 min (CR422 Jouan) to obtain serum.

Serum total calcium concentrations (=calcemia) were measured colorimetrically (Ciba-Corning) using a IEMS Labsystems microplate reader at 540 nm. The differences between the mean values of calcemia in the groups were analysed for variance and by Dunnett's test. The activity of the test compound was calculated as % effect according to the formula:

$$\% \text{ effect} = \frac{Calcemia_{(compound\ group)} - Calcemia_{(PTH\ group)}}{Calcemia_{(PTH\ group)} - Calcemia_{(control\ group)}} \times 100$$

The % effect observed with the compound of formula IIc administered s.c. twice at 30 mg/kg was −97%. This in vivo result shows that the compound is a highly efficient inhibitor of bone resorption.

What is claimed is:

1. (2s)-2-(Adamantan-1-ylmethoxycarbonylamino)-3-(4-(2-(1,4,5,6-tetrahydropyrimidin-2-ylcarbamoyl)ethyl)benzoylamino)propionic acid isopropyl ester of the formula I

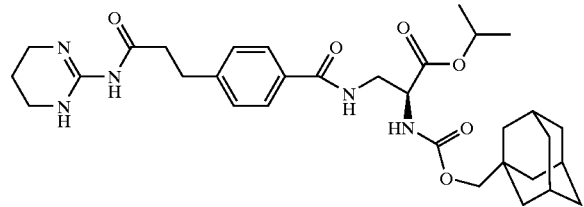

I and its physiologically tolerable salts.

2. (2S)-2-(Adamantan-1-ylmethoxycarbonylamino)-3-(4-(2-(1,4,5,6-tetrahydropyrimidin-2-ylcarbamoyl)ethyl)benzoylamino)propionic acid isopropyl ester hydrochloride of the formula IIc.

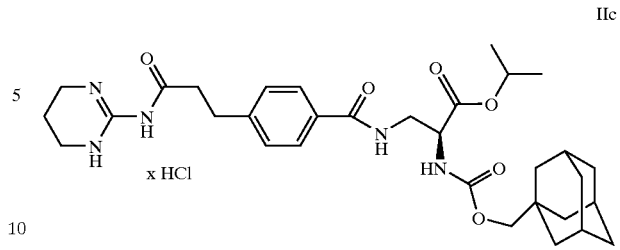

IIc

3. A pharmaceutical composition, comprising the compound of the formula I and/or a physiologically tolerable salt thereof as claimed in claim 1 and a pharmaceutically acceptable carrier.

4. A pharmaceutical composition, comprising the compound of the formula IIc as claimed in claim 2 and a pharmaceutically acceptable carrier.

5. A process for the preparation of the compound of the formula I or a physiologically tolerable salt thereof as claimed in claim 1, comprising the esterification of (2S)-2-(adamantan-1-ylmethoxycarbonylamino)-3-(4-(2-(1,4,5,6-tetrahydropyrimidin-2-ylcarbamoyl)ethyl)benzoylamino) propionic acid or a salt thereof with isopropanol.

6. A process for the preparation of a physiologically tolerable salt of the compound of the formula I as claimed in claim 1, comprising forming a salt from the compound of the formula I and an acid or exchanging the anion in another salt of the compound of formula I.

* * * * *